US009207229B2

(12) United States Patent
Bates et al.

(10) Patent No.: US 9,207,229 B2
(45) Date of Patent: *Dec. 8, 2015

(54) CARTRIDGE FOR STORING BIOSAMPLE PLATES AND USE IN AUTOMATED DATA STORAGE SYSTEMS

(71) Applicant: International Business Machines Corporation, Armonk, NY (US)

(72) Inventors: Allen K. Bates, Tucson, AZ (US); Nils Haustein, Soergenloch (DE); James W. Johnson, Tucson, AZ (US); Stephen L. Schwartz, Tucson, AZ (US); Anna W. Topol, Jefferson Valley, NY (US); Daniel J. Winarski, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/029,667

(22) Filed: Sep. 17, 2013

(65) Prior Publication Data

US 2014/0018265 A1   Jan. 16, 2014

Related U.S. Application Data

(63) Continuation of application No. 13/151,249, filed on Jun. 1, 2011.

(51) Int. Cl.
*G06K 19/06* (2006.01)
*G01N 33/487* (2006.01)
*G11B 23/04* (2006.01)

(52) U.S. Cl.
CPC ........ *G01N 33/48778* (2013.01); *G11B 23/042* (2013.01); *G11B 23/049* (2013.01)

(58) Field of Classification Search
CPC .................. G06K 19/07749; G06K 19/07758
USPC .................................................. 235/492, 493
See application file for complete search history.

(56) References Cited

U.S. PATENT DOCUMENTS

| 3,859,624 A | 1/1975 | Kriofsky et al. |
| 4,650,981 A | 3/1987 | Foletta |
| 4,758,836 A | 7/1988 | Scuilli |
| 4,941,201 A | 7/1990 | Davis |
| 5,320,808 A | 6/1994 | Holen et al. |

(Continued)

OTHER PUBLICATIONS

R. Davies et al., "Engineered Particle Surfaces," Advanced Materials, vol. 10, No. 15, pp. 1264-1270, Published Online: Jan. 26, 1999.

(Continued)

*Primary Examiner* — Daniel St. Cyr
(74) *Attorney, Agent, or Firm* — Zilka-Kotab, PC

(57) ABSTRACT

In one embodiment, a biosample storage cartridge includes an enclosure having a same form factor as a data tape cartridge configured for use in an automated tape library; and a holder disposed in the enclosure. In another embodiment, a biosample storage cartridge includes an enclosure and a holder disposed in the enclosure; the holder is configured to receive one or more biosamples, the cartridge is structurally configured to be picked by a picker of an access robot that is configured to pick a data tape cartridge in an automated tape library. In still another embodiment, an analytical system includes a bioanalysis drive configured to perform bioanalysis on one or more biosamples received from at least one biosample storage cartridge.

18 Claims, 6 Drawing Sheets

(56) References Cited

U.S. PATENT DOCUMENTS

| | | | |
|---|---|---|---|
| 6,201,474 B1 | 3/2001 | Brady et al. | |
| 6,429,016 B1 | 8/2002 | McNeil | |
| 6,637,473 B2 | 10/2003 | Ganz et al. | |
| 6,699,437 B1 | 3/2004 | Astle | |
| 6,875,405 B1 | 4/2005 | Mathus et al. | |
| 7,118,708 B2 * | 10/2006 | Mordekhay | 422/509 |
| 7,142,987 B2 | 11/2006 | Eggers | |
| 7,382,258 B2 | 6/2008 | Oldham et al. | |
| 7,596,251 B2 | 9/2009 | Affleck et al. | |
| 7,635,246 B2 | 12/2009 | Neeper et al. | |
| 7,660,063 B2 * | 2/2010 | Bates et al. | 360/55 |
| 7,663,487 B2 | 2/2010 | Morris et al. | |
| 7,670,553 B2 | 3/2010 | Babson | |
| 7,922,986 B2 | 4/2011 | Byrnard et al. | |
| 7,988,644 B2 * | 8/2011 | Freeman et al. | 600/583 |
| 7,997,682 B2 * | 8/2011 | Silverbrook | 347/32 |
| 8,012,745 B2 * | 9/2011 | Glezer et al. | 435/288.7 |
| 8,337,785 B2 | 12/2012 | Davies et al. | |
| 8,640,964 B2 * | 2/2014 | Bates et al. | 235/492 |
| 2003/0039591 A1 | 2/2003 | Pham et al. | |
| 2003/0087454 A1 | 5/2003 | Schultz et al. | |
| 2005/0180894 A1 | 8/2005 | Petroff et al. | |
| 2006/0161935 A1 | 7/2006 | Johnson et al. | |
| 2009/0117011 A1 | 5/2009 | Morrison | |
| 2010/0105074 A1 | 4/2010 | Covey et al. | |
| 2011/0076670 A1 | 3/2011 | Boday et al. | |
| 2012/0309297 A1 | 12/2012 | Bates et al. | |
| 2012/0309298 A1 | 12/2012 | Bates | |
| 2014/0094114 A1 | 4/2014 | Bates et al. | |

OTHER PUBLICATIONS

Non-Final Office Action from U.S. Appl. No. 13/151,249 dated Feb. 4, 2013.
Final Office Action from U.S. Appl. No. 13/151,249 dated Jul. 17, 2013.
Notice of Allowance and Fee(s) Due from U.S. Appl. No. 13/151,249 dated Sep. 20, 2013.
Non-Final Office Action from U.S. Appl. No. 13/151,247, dated Jun. 18, 2014.
Notice of Allowance from U.S. Appl. No. 13/151,247, dated Jan. 20, 2015.
Non-Final Office Action from U.S. Appl. No. 13/632,021, dated Feb. 13, 2015.
Non-Final Office Action from U.S. Appl. No. 13/151,247, dated May 27, 2015.
ECMA, "Standardizing Information and Communication Systems: Data Interchange on 12,7 mm 384-Track Magnetic Tape Cartridges—Ultrium-1 Format," Standard ECMA-319, Jun. 2001, 13 pages.
Bates et al., U.S. Appl. No. 131151,249, filed Jun. 1, 2011.
Bates et al., U.S. Appl. No. 13/151,247, filed Jun. 1, 2011.
Bates et al., U.S. Appl. No. 13/632,021, filed Sep. 30, 2012.
Boday et al., U.S. Appl. No. 12/888,388, filed Sep. 22, 2010.
Final Office Action from U.S. Appl. No. 13/632,021, dated Aug. 25, 2015.
Notice of Allowance from U.S. Appl. No. 13/632,021, dated Sep. 30, 2015.

* cited by examiner

CARTRIDGE FOR STORING BIOSAMPLE PLATES AND USE IN AUTOMATED DATA STORAGE SYSTEMS

CROSS-REFERENCE TO RELATED APPLICATIONS

This application is a continuation of U.S. patent application Ser. No. 13/151,249 entitled "A Cartridge For Storing Biosample Plates And Use In Automated Data Storage Systems", filed Jun. 1, 2011, which is hereby incorporated by reference.

FIELD OF THE INVENTION

Embodiments of the invention relate to analytical devices and systems, and more particularly, to a cartridge having internal slots for storing biosample plates wherein the cartridge may be stored in the cartridge storage slots of tape library systems and handled by the robotic mechanisms of the tape library systems.

BACKGROUND

Samples of biological matters are often analyzed in bioassay processes to detect the presence of bacteria, viruses, cancer cells, and other substances of interest. The biological samples are typically placed on biosample plates to be analyzed by a biological detection instrument. The detection instrument may record the analysis results of a biosample on a data storage medium such as a computer memory, disk drive, magnetic tape, or compact disk, which may include an identification tag to correlate the biosample with the analysis results.

High-performance computer data storage systems such as optical disc and magnetic tape libraries possess the automation to facilitate the scanning and analysis of biosamples, and to tabulate the resulting analysis data. For example, these systems may analyze the biosamples using magnetic tape read heads to detect magnetized nanoparticles attached to the biosamples. The biosamples and analysis data may be stored in different locations following the analysis, which make it difficult to correlate the biosamples with the corresponding data when needed. For a large number of biosamples and biosample plates, the task of correlating the biosamples to their data becomes even more complex. It is desirable to exploit the use of automation functions available in computer tape library systems to facilitate the correlation and management of biosample plates and biosample analysis data.

BRIEF SUMMARY OF THE DISCLOSURE

The disclosure relates to a biosample storage cartridge includes an enclosure having a same form factor as a data tape cartridge configured for use in an automated tape library; and a holder disposed in the enclosure, in one embodiment. The holder includes a plurality of slots, each slot being configured to receive a biosample plate.

In another embodiment, a biosample storage cartridge includes an enclosure and a holder disposed in the enclosure; the holder is configured to receive one or more biosamples, the cartridge is structurally configured to be picked by a picker of an access robot that is configured to pick a data tape cartridge in an automated tape library.

In still another embodiment, an analytical system includes a bioanalysis drive configured to perform bioanalysis on one or more biosamples received from at least one biosample storage cartridge.

The details of the exemplary embodiments of the disclosure, both as to its structure and operation, are described below in the Detailed Description section in reference to the accompanying drawings. The Brief Summary is intended to identify key features of the claimed subject matter, but it is not intended to be used to limit the scope of the claimed subject matter.

DETAILED DESCRIPTION OF THE DISCLOSURE

Embodiments of the disclosure relate to biosample cartridges that include internal storage slots for holding biosample plates that may be scanned, analyzed, and handled by a computer tape drive and stored in the cartridge storage slots of an automated tape library. The biosample plates may contain biological samples that are written to by electromagnetic tape heads. They may then be scanned and read from by anisotropic magneto-resistive (AMR), giant magnetoresistive (GMR) or tunnel magnetoresistive (TMR) read elements to detect the presence of target substances or micro-organisms in the biological samples. The biosample plates may have a width of 12.65 mm (½ inch), which is the width of commonly used magnetic data tapes. The biosample plate storage cartridge may have the same form factor as data tape cartridges used in automated data storage libraries and thus may be conveniently accessed, manipulated, and processed by robotic mechanisms in these libraries. The biosample cartridge may be handled through the same library internal-external mail slot as a tape cartridge. The same tape automation mechanisms and processes used in modern tape libraries may be used for long-term biological-archival storage of the biosamples contained in the biosample cartridge.

The biosample storage cartridge may include a plate holder to retain a plurality of biosample plates in the cartridge when the cartridge is moved, for example by a robotic picker in a tape library, as well as when the cartridge is in storage. The plate holder may have a plurality of parallel storage slots for receiving the biosample plates, which may be in the form of thin strips of glass or a similar material. The biosample plate storage cartridge is described in detail below with reference to FIGS. 1-3.

Figure 1:
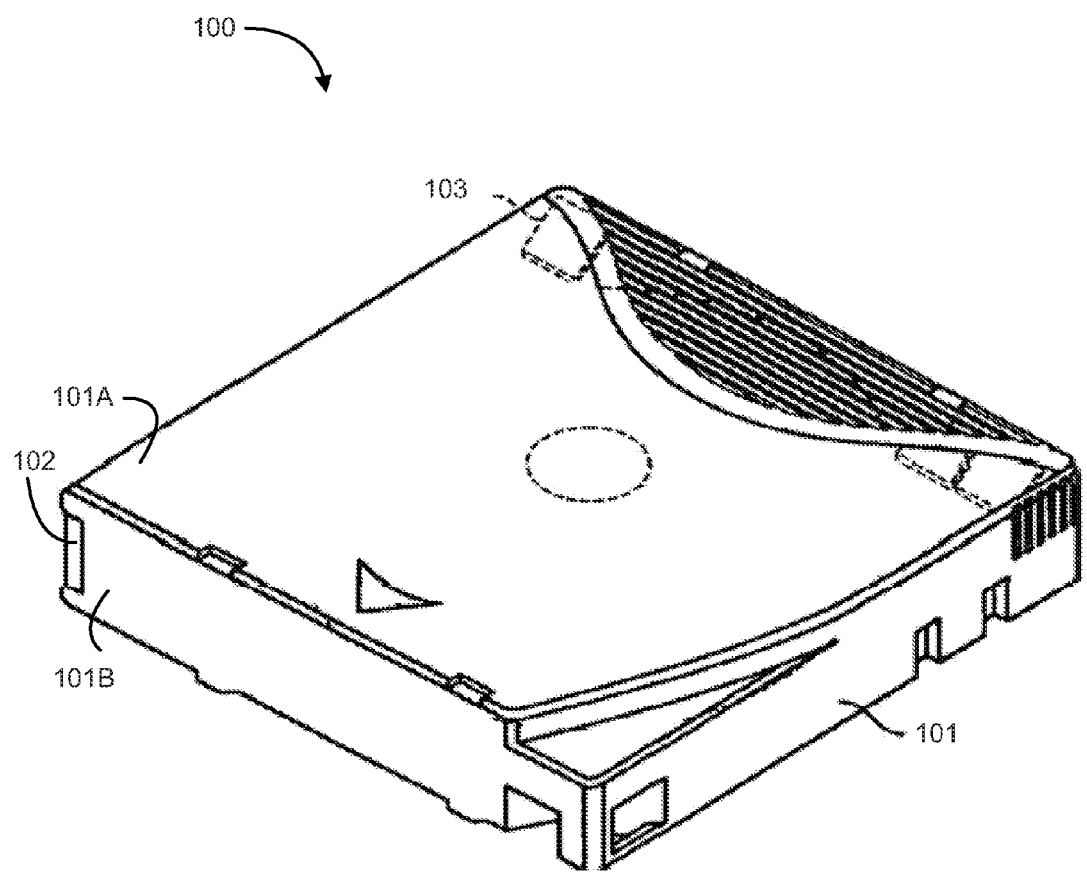
FIG. 1 illustrates an exemplary cartridge for storing biosample plates, in accordance with an embodiment of the invention.

Referring to the drawings and in particular to FIG. 1, there is illustrated an exemplary biosample plate storage cartridge 100 in which a plurality of slots may be provided to hold the biosample plates. The biosample plate storage cartridge 100 comprises an enclosure 101, which may include one or more parts. The cartridge 100 may have a movable side door 102 that can be slid open, for example by a tape drive, to gain access to the interior space of the cartridge 100. The tape dive may be adapted to perform biosample analysis. In one embodiment, the biosample plate storage cartridge 100 may comprise atop shell 101A and a bottom shell 101B wherein the top shell 101A is removably affixed to the bottom shell 101B by screws or other fasteners. Alternatively, the biosample plate storage cartridge 100 may have a front, top, or rear door that is movable to provide access to the interior space of the cartridge.

The biosample plate storage cartridge 100 may have the same size and exterior configuration as a magnetic tape storage cartridge based on LTO (Linear Tape Open) technology, the IBM TS1130 magnetic tape data storage cartridge, or the Oracle T10000 tape cartridge. In an alternate embodiment, older IBM single-reel tape cartridges could be used, such as the 3480, 3490, and 3590 tape cartridges. In a data storage cartridge, a data storage media such as a magnetic tape, may be mounted on a tape reel and occupy the space inside the biosample storage cartridge 100 rather than the biosample plates. Such a tape data storage cartridge may comprise a cartridge brake release button to allow the tape reel to freely rotate once the cartridge is loaded into a data storage drive.

The biosample plate storage cartridge 100 may further include one or more cartridge memories 103 for storing identification information about the biosample storage cartridge 100, data related to the biosample plates, and analysis data associated with the biosamples stored in the biosample storage cartridge 100. Each cartridge memory 103 may comprise a transponder having a wireless interface, which is retained in the cartridge 100, for example, by being encapsulated by the cartridge when it is assembled. The encapsulation process is understood by those of skill in the art as applied to a single cartridge memory.

Figure 2:
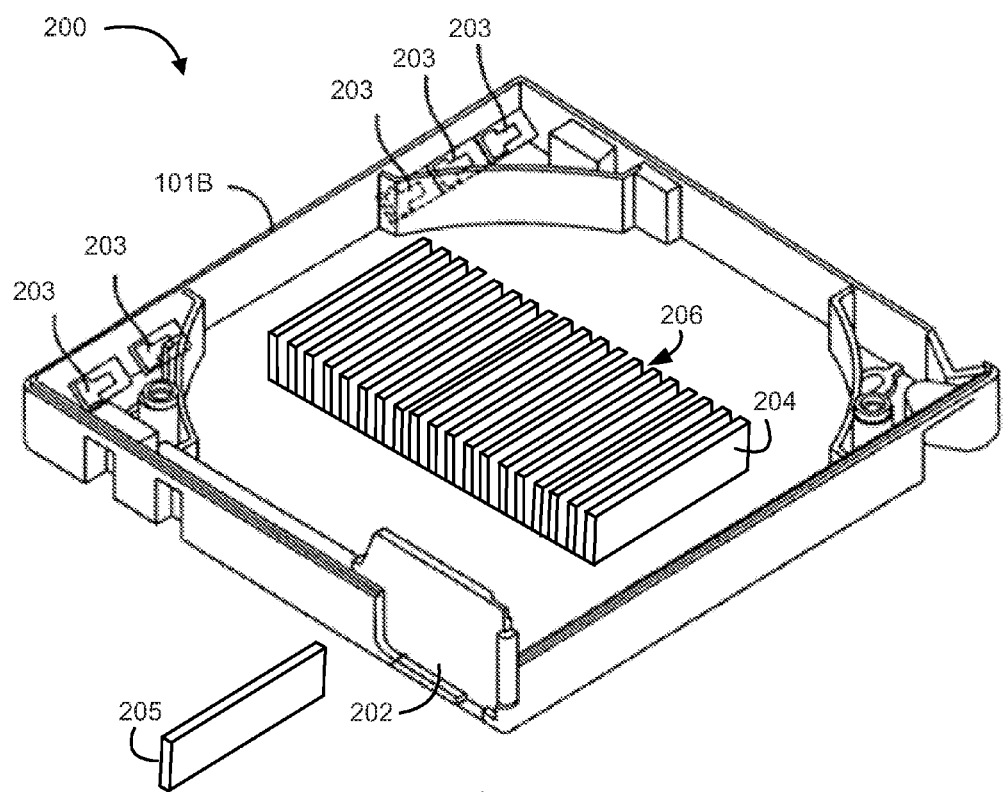
FIG. 2 illustrates a biosample storage cartridge with its cover opened to show the storage slots for holding biosample plates in the cartridge, in accordance with an embodiment of the invention.

FIG. 2 illustrates a biosample plate storage cartridge 200 with its cover removed to show the storage slots for holding biosample plates, in accordance with an embodiment of the invention. The biosample storage cartridge 200 comprises a plate holder 204 for holding a plurality of biosample plates 205. The plate holder 204 may be an integral part of the biosample storage cartridge 200 or a separate part that is attached to the data storage cartridge 200 by fasteners or adhesive. The plate holder 204 may comprise a plurality of parallel slots 206 to hold the biosample plates 205 in place and prevent the biosample plates 205 from separating from the plate holder 204 when the storage cartridge 200 is being moved. Movable door 202 is shown at the bottom corner of the cartridge 200.

In one embodiment, the width of the slots 206 is slightly larger than the thickness of the biosample plates 205 to snugly accommodate the biosample plates 205 and firmly retain the biosample plates 205 in the slots 206 by friction. In one embodiment, the biosample plates 205 may have a thickness of 1.0 mm and the width of the slots 206 is slightly larger than the thickness of the biosample plates. For example, for a thickness of 1.0 mm for the biosample plates, the width of the slots may be in the range of 1.05-1.2 mm. In an alternate embodiment, the material containing slots 206 is elastic, such as a polymer or elastomer, and the width of slots 206 is slightly smaller, ranging from 0.90 mm to 1.0 mm.

The biosample plate storage cartridge 200 may include one or more cartridge memory 203 for storing data related to the biosample cartridge 200, for example, the identification of the biological samples, biosample plates, analysis data on the biological samples, and relevant dates such as creation dates and analysis dates. The cartridge memory 203 may be in communication with a wireless communication interface to send information to and receive information from a remote transceiver, for example, in a tape library system that handles the biosample plate storage cartridge 200.

Although FIGS. 1-2 illustrate a biosample plate storage cartridge that has the same form factor as a single reel magnetic tape cartridge, the biosample storage cartridge may have the same form factor as a dual reel cartridge, such as the IBM 3570 cartridge. In a dual reel cartridge, the magnetic tape is fed between the two reels of the cartridge. Such a biosample plate storage cartridge may comprise a biosample plate holder 204 in the space occupied by the two tape reels, as similarly described with reference to FIGS. 1-2.

Figure 3:
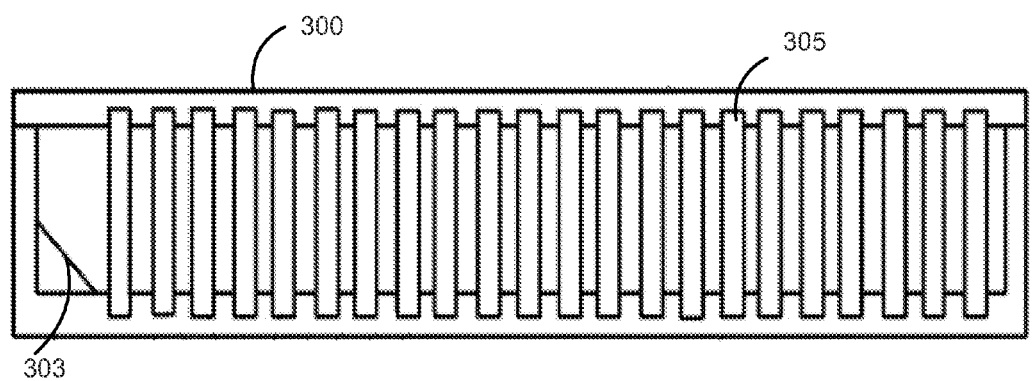
FIG. 3 illustrates a cross-sectional side view of a biosample plate storage cartridge with the slots for holding biosample plates, in accordance with an embodiment of the invention.

FIG. 3 illustrates a cross-sectional side view of a biosample plate storage cartridge 300 with storage slots for holding the biosample plates 305, in accordance with an embodiment of the invention. The biosample plates 305 are retained by the slots in the biosample storage cartridge 300 as described with reference to FIGS. 1-2. Cartridge memory 303 is shown at a generally 45 degree angle, so that the memory may be wirelessly accessed by either the robotic picker in the automated library or the tape drive modified to perform bio-analysis.

Figure 4:
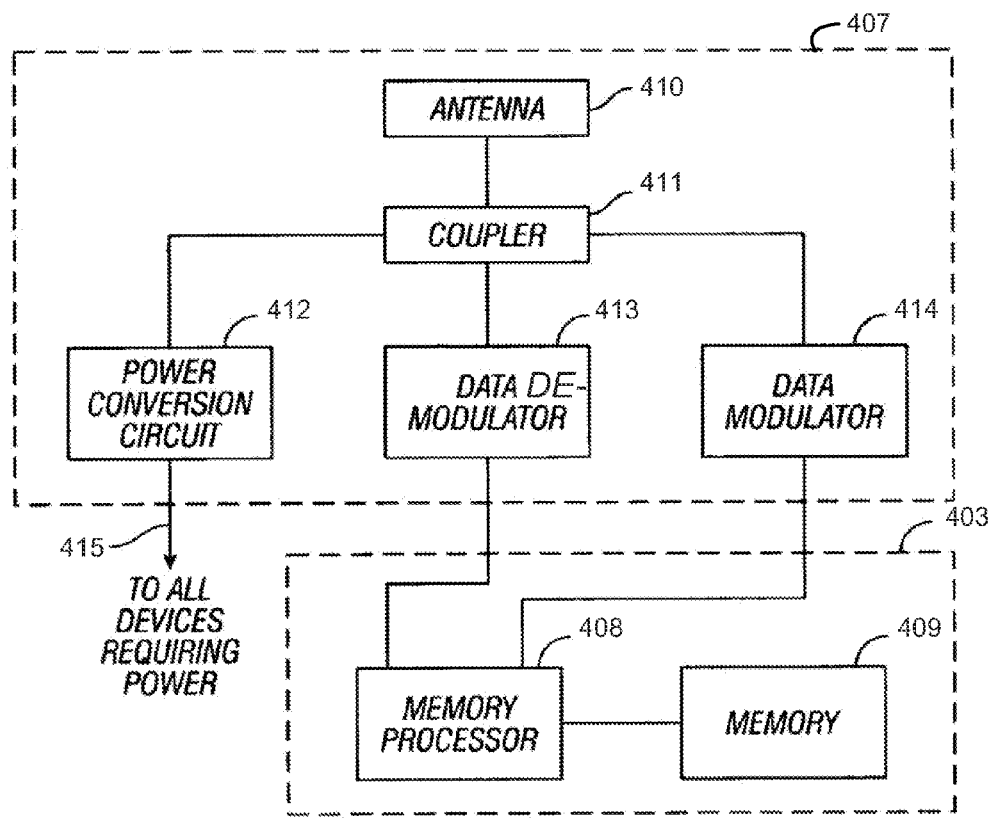
FIG. 4 illustrates a block diagram of a memory component and a wireless communication interface, which may be part of a biosample plate storage cartridge, for storing and transferring information related to the cartridge, in accordance with an embodiment of the invention.

FIG. 4 illustrates a block diagram of the functional components of a memory component 403 and a wireless communication interface 407, which may be part of a biosample storage cartridge 100, such as cartridge memories 103, 203, and/or 303. The memory component 403 may store information about the biosample cartridge, biosample plates in the cartridge, and biosamples on the biosample plates. The Memory component 403 may comprise a nonvolatile memory 409, such as an electrically erasable programmable read-only memory (EEPROM), a phase-change memory, flash memory, NOR memory, or a NAND memory arranged to operate in a low power environment. Memory component 403 also may comprise memory processor 408, such as logic or a microprocessor chip, for example, an Intel Pentium™ chip arranged to operate in a low power environment, such as a portable computer.

The memory processor 408 may have computer readable program code embodied therein, including suitable security and encryption/decryption algorithms, and the logic for accessing and operating the memory component 403. The memory component 403 may comprise a nonvolatile storage 409, as is known to those of skill in the art. The nonvolatile storage 409 may comprise a separate chip attached to the logic or memory processor 408, or may comprise a portion of the same chip. The computer readable program code may be stored in a nonvolatile internal memory of the processor 408 or in the nonvolatile memory 409, and loaded into the processor 408. Alternatively, the memory component 403 may be operated by a control system or processor of an analytical system that uses the biosample storage cartridge 100.

In the illustrated embodiment, the wireless communication interface 407 may be a radio frequency (RE) wireless interface. An example of an RE wireless interface is described in U.S. Pat. No. 4,941,201. A high frequency inductive wireless interface may also be employed, which is of sufficiently high frequency so that it does not adversely affect magnetic storage media that may be present in a tape library system that handles the biosample storage cartridge. Examples of high frequency inductive wireless interfaces are described in U.S. Pat. No. 4,650,981, U.S. Pat. No. 4,758,836, and U.S. Pat. No. 3,859,624.

The wireless communication interface 407 includes an antenna 410 for receiving an RF signal from an RF interface of either a tape drive modified to perform bio-analysis or a robotic picker that moves the biosample plate storage cartridge 300 in a tape library system. The antenna 410 may be positioned at an angle in the range of 30-60 degrees for optimal reception of the RF signal, e.g., at 45 degrees as shown for the cartridge memory 303 of FIG. 3. The antenna 410 may be a quarter wave antenna, a fractal antenna, or the inductor of an inductor-capacitor oscillator. A coupler 411 supplies the received signal to a power conversion circuit 412 and to a data demodulator 413. The power conversion circuit 412 converts the received signal to a power current, supplying the current on line 415 to all devices on the biosample storage cartridge 300, including the memory component 404, the data demodulator 413, and a data modulator 414. The received signal from antenna 410 may be encoded. The data demodulator 413 receives the incoming coded signal from coupler 411 and demodulates the signal to provide data signals to the memory component 404 and for writing to memory 409. Data signals being read from memory 409 and memory component 404 are provided to the data modulator 414 which encodes the signals for transmission by coupler 411 and antenna 410 to an RF interface, which may be in either the robotic picker of the tape library system that handles the biosample plate storage cartridge 300 or in the tape drive modified to perform bio-analysis.

Figure 5:
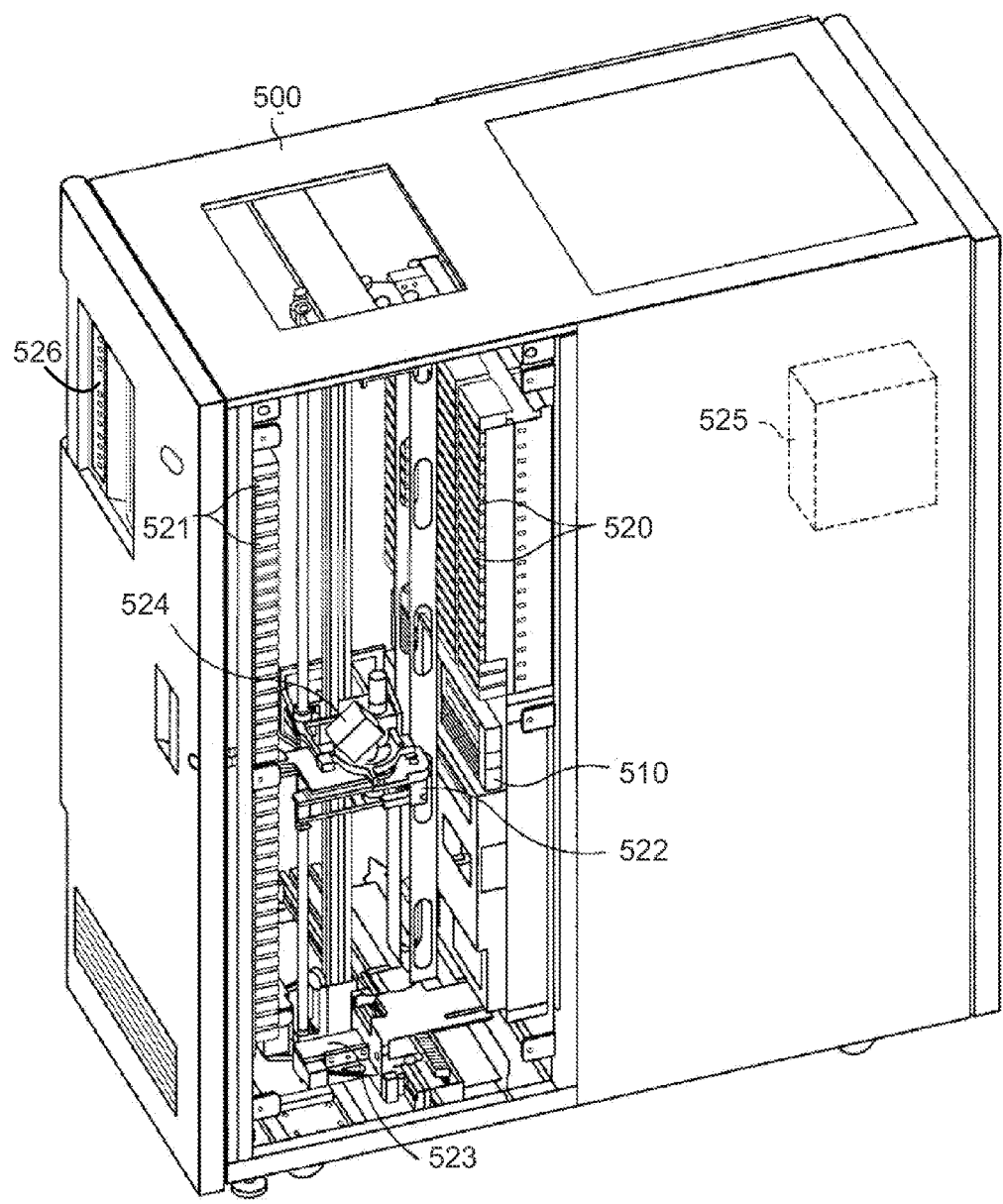
FIG. 5 illustrates an automated data storage tape library that may be used with the disclosed biosample plate storage cartridge, in accordance with an embodiment of the invention.

FIG. 5 illustrates an automated data storage tape library 500 that may be used with the biosample plate storage cartridge shown in FIGS. 1-4, in accordance with an embodiment of the invention. The data storage tape library 500 is an automated tape library that may include a number of tape drives 510 for reading and writing data on magnetic tape media, such as single-reel or two-reel magnetic tape cartridges. Examples of the library 500 include IBM TS3400™ and TS3500™ Tape Libraries, IBM TotalStorage™ 3494 Tape Libraries, and IBM 3952™ Tape Frames Model C20, which store magnetic tape cartridges and use IBM TS1130™ tape drives. Other examples of the library 500 include IBM TS3310™ and TS3100/3200™ tape libraries which store magnetic tape cartridges and use IBM LTO (Linear Tape Open) tape drives. Tape drives modified to perform bio-analysis accept cartridge 100, 200, 300 from the robotic picker, withdraw a biosample plate through door 202 of cartridge 200, and perform the bio-analysis.

A plurality of cartridges 520 are stored in banks or groups of cartridge storage slots 521. Cartridges 520 may comprise tape media for data storage, tape substrate for biosamples, or biosample plates 205 and 305 for bio-analysis. Tape media may encompass a variety of media, such as that contained in magnetic tape cartridges, magnetic tape cassettes, and optical ape cartridges, in various formats. For universal reference to any of these types of media, the terms "tape media" or "media" are used herein, and any of these types of containers are referred to as "tape cartridges" or "cartridges" herein. An access robot 523, including a cartridge picker 522 and a bar code reader 524 mounted on the cartridge picker 522, transports a selected cartridge 520 between a cartridge storage slot 521 and a drive 510. Bar code reader 524 is mounted directly on picker 522 so that the library 500 can check the bar code on cartridge 520 before picking the cartridge and transporting it to a drive 510, storage slot 521, or import/export mail slot 526.

The automated tape library 500 further has a library controller 525 which includes at least one microprocessor. The library controller 525 may serve to provide an inventory of the cartridges 520 and to control the library 500. Typically, the library controller 525 has suitable memory and data storage capability to control the operation of the library 500. The library controller 525 controls the actions of the access robot 523, cartridge picker 522, and bar code reader 524. Barcode reader 524 may read a barcode from cartridge 100, 200, or 300. The library controller 525 is interconnected through an interface to one or more host processors, which provides commands requesting access to a particular biosample plate, a tape media, or a cartridge in particular storage slots. A host, either directly or through the library controller, controls the actions of the drives 510 which either perform data IO with tape media or, if suitably modified, perform bio-analysis on the biosamples stored on plates 205 and 305. Commands for accessing data or locations on the tape media and biosample plates, and information to be recorded on or to be read from selected tape media and biosample plates, are transmitted between the drives 510 and the host. The library controller 525 is typically provided with a database for locating the cartridges 520 in the appropriate storage slots 521 and for maintaining the cartridge inventory.

Library 500 also includes an import/export mail slot 526, which is a portal allowing cartridges 520 to be entered into or removed from library 500. Since cartridges 520 have a generally identical exterior dimensions regardless of whether they hold data tape or biosample plates, cartridges 520 may enter library 500 through import/export mail slot 526, picked up by picker 522 and transported to either cartridge-storage slot 521 or drives 510. Drives 510 would have a common cartridge loader mechanism, whether the drive is a data drive or a bio-analysis drive, because of cartridges 520 having identical exterior dimensions. Similarly picker 522 may pick cartridge 520 from a drive 510 or cartridge-storage slot 521 and place it in import/export mail slot 526 for removal from library 500. In an alternate embodiment, biosample cartridges 520 are a different color from cartridges containing digital data, as well as containing information regarding their intended purpose in memories 103, 203, and 303.

Figure 6:
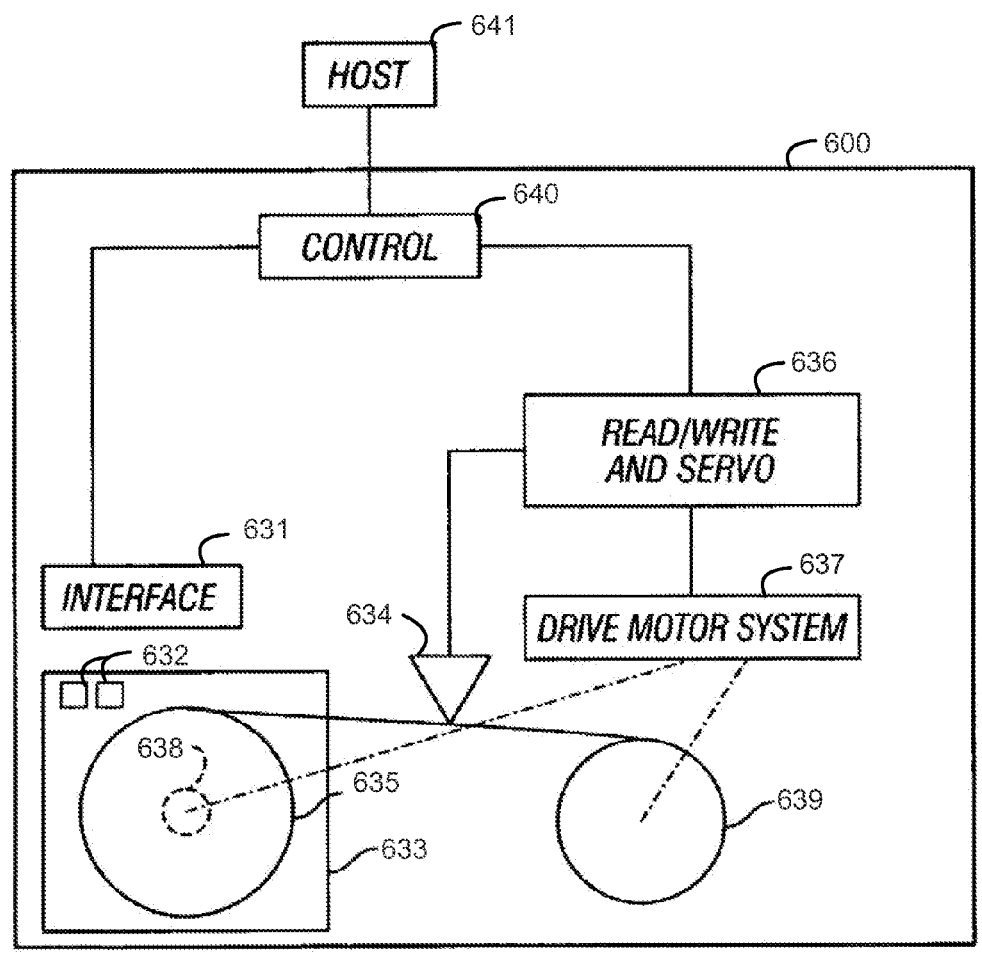
FIG. 6 illustrates a block diagram of the functional components in a data storage tape drive that may be used for analyzing a biosample and storing biosample identification and analysis data, in accordance with an embodiment of the invention.

FIG. 6 illustrates a block diagram of the functional components in a tape drive that may be used for analyzing a biosample and storing biosample identification and analysis data, in accordance with an embodiment of the invention. The magnetic tape drive 600 comprises a memory interface 631 for reading information from and writing information to one or more of the cartridge memory 632 of the magnetic tape cartridge 633, for example, in a contactless manner.

A read/write system is provided for reading and writing information to the data storage media, such as magnetic tape, or nanoparticles on the biosample plates 205 and 305, and may comprise a read/write head 634 with a servo system for moving the head laterally of the magnetic tape 635 or a biosample plate (not shown in FIG. 6). The servo system may comprise a read/write and servo control 636 and a drive motor system 637 which moves the magnetic tape 635 between the cartridge reel 638 and the take up reel 639 and across the read/write head 634. The read/write and servo control 636 controls the operation of the drive motor system 637 to move the magnetic tape 635 across the read/write head 634 at a desired velocity. The read/write and servo control 636 may determine the location of the read/write head 634 with respect to the magnetic tape 635.

In one example, the read/write head 634 and read/write and servo control 636 employ servo signals on the magnetic tape 635 to determine the location of the read/write head 634, and in another example, the read/write and servo control 636 employs at least one of the reels, such as by means of a tachometer, to determine the location of the read/write head 634 with respect to the magnetic tape 635. The read/write head 634 and read/write and servo control 636 may comprise hardware elements and may comprise any suitable form of logic, including a processor operated by software, or microcode, or firmware, or may comprise hardware logic, or a combination. In an alternate embodiment, tape 635 is simply a flexible substrate, such as a MYLAR™ substrate, and biosamples are stored directly on this substrate and wound around reel 638 in cartridge 633.

A control system 640 communicates with the memory interface 631, and communicates with the read/write system, e.g., at read/write and servo control 636. The control system 640 may comprise any suitable form of logic, including a processor operated by software, or microcode, or firmware, or may comprise hardware logic, or a combination thereof. The control system 640 typically communicates with one or more host systems 641, and operates the data storage drive 600 in accordance with commands originating at a host. Alternatively, the data storage drive 600 may form part of a subsystem, such as a library, and may also receive and respond to commands from the subsystem.

As illustrated, the data storage drive 600 provides information to a cartridge memory 632 of the magnetic tape cartridge 633, and provides data to the magnetic tape 635 of the magnetic tape cartridge 633.

In one embodiment, the data storage tape drive 600 may function as an analytical system for scanning the biosample plates 205, 305 and analyzing biological samples deposited on the biosample plates 205, 305 to detect the presence of target antigens or substances. The magneto-resistive (MR) heads of the read/write head 634 in data storage drive 600 may act as the scanners for reading data from the biosamples. Write heads of read/write head 634 may magnetize nanoparticles used to tag the biosamples which are subsequently read or detected by the MR heads. For example, an MR read/write head 634 may be used to detect micro-organisms and antigens that are attached to magnetized nanoparticles.

An MR read-write head may scan a large number of biosamples deposited on a magnetic tape media as the MR read-write head traverses the tape media a high speed. The tape drive electronics may then process the signals from the read-write MR head to detect the presence of target micro-organisms or antigens in the biosamples. Such as bio-assay process is described, for example, in the commonly-assigned US patent application entitled "Detection Of Analytes Via Nanoparticle-Labeled Substances With Electromagnetic Read-Write Heads", Ser. No. 12/888,388, herein incorporated by reference in its entirety.

Figure 7:
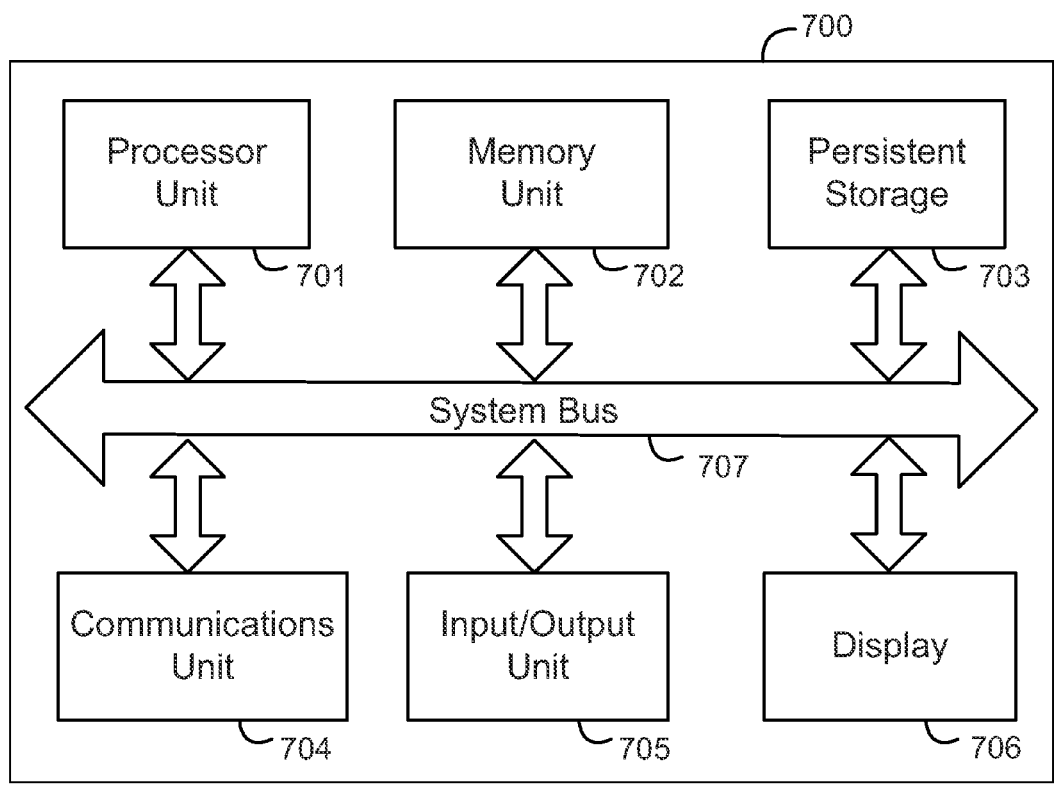
FIG. 7 illustrates a block diagram of the functional components in a computer, which may be incorporated into a data storage tape library and a cartridge memory to provide control and processing functions, in accordance with an embodiment of the invention.

FIG. 7 illustrates a block diagram of a representative computer system, some of which may be incorporated in a data storage tape library and a cartridge memory to provide control and processing function, for providing aspects of the disclosure. Data processing system 700 includes a processor 701, a memory 702, a persistent storage 703, a communication interface 704, an input/output unit 705, a display 706 and a system bus 707. Computer programs are typically stored in persistent storage 703 until they are needed for execution by an operating system running in memory 702. Persistent storage 703 may comprise one or more hard disk drives and multiple hard disk drives may be organized into a RAID, CD (Compact Disk) drives, DVD (Digital Versatile Disk) drives, BD (Blu-Ray) drives, SSD (Solid State Drives), and solid state memory. At that time, the programs are brought into the memory 702 so that they can be directly accessed by the processor 701. The processor 701 selects a part of memory 702 to read and/or write by using an address that the processor 701 gives to memory 702 along with a request to read and/or write. Usually, the reading and interpretation of an encoded instruction at an address causes the processor 701 to fetch a subsequent instruction, either at a subsequent address or some other address. The processor 701, memory 702, persistent storage 703, communication interface 704, input/output unit 705, and display 706 interface with each other through the system bus 707.

The subject matter described above is provided by way of illustration only and should not be construed as limiting. Various modifications and substitutions of the described components and operations can be made by those skilled in the art without departing from the spirit and scope of the present disclosure defined in the following claims, the scope of which is to be accorded the broadest interpretation so as to encompass such modifications and equivalent structures.

What is claimed is:

1. A biosample storage cartridge, comprising:
an enclosure having a same form factor as a data tape cartridge that is configured for use in an automated tape library; and
a holder disposed in the enclosure,
wherein the holder comprises a plurality of slots, each slot being configured to receive a biosample plate,
wherein the form factor includes a same size and a same exterior shape as an existing magnetic tape storage cartridge configuration, and
wherein the existing magnetic tape storage cartridge size and shape is based on a configuration selected from a group consisting of: a Linear Tape Open (LTO) tape cartridge, a single-reel tape cartridge, and a dual-reel tape cartridge.

2. The biosample storage cartridge as recited in claim 1, further comprising a memory coupled to the cartridge.

3. The biosample storage cartridge as recited in claim 2, further comprising a wireless communication interface coupled to the memory.

4. The biosample storage cartridge as recited in claim 3, the wireless interface comprising an antenna configured to receive an RF signal from an RF interface of one or more of:
an access robot configured to transport the cartridge; and
a drive configured to perform bioanalysis on one or more biosample plates in the holder.

5. A biosample storage cartridge, comprising:
an enclosure having a same form factor as a data tape cartridge that is configured for use in an automated tape library; and
a holder disposed in the enclosure,
wherein the holder is configured to receive one or more biosamples,
wherein the cartridge is structurally configured to be picked by a picker of an access robot that is configured to pick a data tape cartridge in an automated tape library,
wherein the form factor includes a same size and a same exterior shape as an existing magnetic tape storage cartridge configuration, and
wherein the existing magnetic tape storage cartridge size and shape is based on a configuration selected from a group consisting of: a Linear Tape Open (LTO) tape cartridge, a single-reel tape cartridge, and a dual-reel tape cartridge.

6. The biosample storage cartridge as recited in claim 5, the enclosure further comprising a movable door,
wherein the cartridge is further configured to provide a drive access to the biosamples via the movable door, and
wherein the drive is a tape drive.

7. The biosample storage cartridge as recited in claim 5, wherein the biosamples are disposed on one or more biosample plates.

8. The biosample storage cartridge as recited in claim 7, wherein the holder comprises a plurality of slots, each slot being configured to retain one of the biosample plates.

9. The biosample storage cartridge as recited in claim 5, wherein the holder comprises a tape media substrate, and
wherein the biosamples are disposed on the tape media substrate.

10. The biosample storage cartridge as recited in claim 9, the holder comprising at least one reel configured to hold the tape media substrate.

11. An analytical system, comprising:
a bioanalysis drive configured to perform bioanalysis on one or more biosamples received from at least one biosample storage cartridge comprising an enclosure having a same form factor as a data tape cartridge that is configured for use in an automated tape library,
wherein the form factor includes a same size and a same exterior shape as an existing magnetic tape storage cartridge configuration, and
wherein the existing magnetic tape storage cartridge size and shape is based on a configuration selected from a group consisting of: a Linear Tape Open (LTO) tape cartridge, a single-reel tape cartridge, and a dual-reel tape cartridge.

12. The analytical system as recited in claim 11, further comprising:
a housing; and
a data drive configured to:
write data to a data storage medium of one or more data storage cartridges; and
read data from the data storage medium,
wherein the bioanalysis drive and data drive reside in the housing.

13. The analytical system as recited in claim 11, the bioanalysis drive further comprising a common cartridge loader configured to:
load a data storage cartridge comprising a data storage medium into the bioanalysis drive; and
load the at least one biosample storage cartridge comprising the one or more biosamples into the bioanalysis drive.

14. The analytical system as recited in claim 11, wherein the one or more biosamples are disposed on one or more biosample plates, and
wherein the bioanalysis drive is further configured to retrieve the biosample plates from the at least one biosample storage cartridge.

15. The analytical system as recited in claim 11, wherein the one or more biosamples are disposed on a magnetic tape substrate, and
wherein the bioanalysis drive is further configured to access the magnetic tape substrate.

16. The analytical system as recited in claim 11, further comprising:
a plurality of storage slots, each storage slot being configured to interchangeably receive:
at least one data storage cartridge; and
at least one of the biosample storage cartridges.

17. The analytical system as recited in claim 16, further comprising an access robot configured to:
transport one or more of the biosample storage cartridges between the bioanalysis drive and the storage slots using a picker;
wherein the picker is configured to interchangeably pick the biosample storage cartridges and the at least one data storage cartridge from the storage slots using an identical operation.

18. The analytical system as recited in claim 11, wherein the bioanalysis comprises detecting presence of one or more of: a target antigen and a target microorganism.

* * * * *